United States Patent [19]
Van Der Heiden et al.

[11] Patent Number: 5,879,318
[45] Date of Patent: Mar. 9, 1999

[54] METHOD OF AND CLOSED SYSTEM FOR COLLECTING AND PROCESSING UMBILICAL CORD BLOOD

[75] Inventors: Johannes Van Der Heiden; Else Johanna Meijer, both of Emmen, Netherlands

[73] Assignee: NPBI International B.V., Emmer-Compascum, Netherlands

[21] Appl. No.: 912,501

[22] Filed: Aug. 18, 1997

[51] Int. Cl.[6] ................................................. A61M 37/00
[52] U.S. Cl. ............................. 604/6; 604/410; 604/416; 210/767; 210/806
[58] Field of Search ................................. 604/4–6, 27, 28, 604/317, 403, 408, 410, 416; 606/120–124; 128/573, 577, 580, 897, 898; 204/450, 518, 543; 210/806, 767; 435/2; 436/175, 177, 178

[56] References Cited

U.S. PATENT DOCUMENTS

| | | |
|---|---|---|
| 3,489,145 | 1/1970 | Judson et al. . |
| 3,892,236 | 7/1975 | Djerassi . |
| 4,111,199 | 9/1978 | Djerassi . |
| 5,114,672 | 5/1992 | Knippscheer et al. . |
| 5,342,328 | 8/1994 | Grossman et al. ...................... 604/317 |
| 5,415,665 | 5/1995 | Hessel et al. ............................... 604/4 |
| 5,520,699 | 5/1996 | Hessel et al. ............................... 604/4 |

*Primary Examiner*—Aaron J. Lewis
*Assistant Examiner*—David J. Cho
*Attorney, Agent, or Firm*—Herbert Dubno

[57] ABSTRACT

A closed sterile bag system contains at least two separate compartments with communication between them temporarily blocked and with one of the compartments containing an erythrocyte sedimentation solution. The umbilical cord blood is collected and contacted with an anticoagulant whereupon the blockage is removed and the erythrocyte sedimentation solution is caused to contact the blood all within the closed sterile system.

15 Claims, 7 Drawing Sheets

METHOD OF AND CLOSED SYSTEM FOR COLLECTING AND PROCESSING UMBILICAL CORD BLOOD

SPECIFICATION

1. Field of the Invention

Our present invention relates to a method of and to a closed system for collecting and processing umbilical cord blood and, more particularly, to a closed blood-collection bag system with an erythrocyte sedimentation solution in a compartment of that closed system.

2. Background of the Invention

Stem cells are the cells in the bone marrow and in the peripheral blood that are able to create new blood cells. They can be used for the treatment of many congenital and acquired hematological diseases as, for example, cancer. They can be harvested from at least three sources. Besides the already mentioned bone marrow and peripheral blood, umbilical cord blood is an increasingly important source for stem cells as well. It offers several advantages over the other stem cell sources. Cord blood is easy and cheap to collect without risk for the donor and has a low incidence of graft-versus-host disease.

Standard blood bag systems for the collection and processing of peripheral blood consist of at least a collection bag and a collection needle, connected via a tube.

The collection bag can contain an anticoagulant such as a citrate-phosphate-dextrose solution (CPD), citrate-phosphate-dextrose with adenine (CPDA), sodium citrate solution or an anticoagulant citrate-dextrose solution (ACD) or heparin.

To aid blood processing and improve the safety, processing bags for various blood components are usually part of the sterile blood bag system. A red cell storage solution may be incorporated into one of the processing bags. Both the collection bag and the processing bags can be equipped with ports and break connectors. The ports are used for the addition or extraction of materials to or from the inside of the bag. A break connector is used to temporarily close a tube or the entrance of a bag. It is part of the sterile internal fluid path and can be opened (irreversibly) from the outside when needed. Blood bag systems for the collection and processing of peripheral blood are described in several patents.

Currently, most cord blood donations are collected in standard blood bag systems. The system is adjusted for the collection of cord blood by draining part of the anticoagulant solution from the collection bag and sealing and removing the processing bags from the system. There are also specially designed blood bag systems for the collection of cord blood. One such system is NPBI's CB Collect™, shown in FIG. 1. This system consists of a collection bag 1, two needles 2, and two small bags 3 each filled with the anticoagulant CPD 4.

Cord blood stem cells can be banked relatively easy. Therefore, in many countries the cord blood of new-born babies is being collected and special Cord Blood Banks are being developed. One of the obstacles for establishing Cord Blood Banks is the storage space needed for the frozen cord blood units. At the moment, many cord blood units are frozen as a whole, without volume reduction. However, this is not the preferred way as it requires the availability of large storage capacity. Also, large volumes of (potentially toxic) cryoprotectant are added to the blood unit and may be infused in patients later. To overcome these obstacles, several protocols for the purification of cord blood are used or are under investigation. Blood, both peripheral and from the umbilical cord, consists of three major components, namely red cells or erythrocytes, white cells or leukocytes, and plasma. The stem cells reside in the leukocyte fraction. The purpose of the purification of cord blood is to reduce the volume of plasma and to remove the red cells, which constitute the majority of the cells in the blood.

A frequently employed method for the purification of cord blood after collection is by sedimentation of the red blood cells. The collection starts with bringing the required volume of anticoagulant into a collection bag. Next, the cord is disinfected at the collection spot. Subsequently, the vein in the cord is punctured with the collection needle and the cord blood is collected while mixing it with the anticoagulant solution. After collection, samples of the blood are taken and the blood is ready for sedimentation. A port of the bag is opened and a volume of HES solution is added to the contents of the bag. The added volume is chosen in such a way that it creates a final concentration of 1.2% HES (hydroxyethylstarch) solution in the blood. The volume therefore depends upon the actual volume of cord blood collected. On average, 50 to 100 ml of blood can be collected from an umbilical cord. A volume exceeding 200 ml is rarely collected.

After addition of HES solution the sedimentation of the red blood cells starts. Usually, sedimentiaton is aided by a short centrifuge spin of approximately fifty times the gravitational force (50 g) during five minutes. The centrifugation causes the blood to separate in two layers: the lower layer consisting of the sedimented red cells with HES solution and the upper layer being leukocyte-rich plasma depleted of most of the red cells. This leukocyte-rich plasma contains the precious stem cells. It is extracted from the collection bag into a processing bag. To further reduce the volume, the leukocytes in the plasma are spun down during a second centrifuge spin. Again two layers are formed by the centrifugation. The upper layer now mainly consists of plasma while the lower layer contains the leukocytes. After the plasma is extracted the blood cell preparation is reduced to a volume of only several milliliters for cryopreservation.

The sedimentation of red cells by HES or dextran (with a molecular weight of approx. 70,000 and higher), usually in a concentration between 1 and 4%, is commonly known in the art. Other agents that are used to sedimentate red blood cells include ficoll, gum arabic, polyvinyl pyrrolidone, methyl cellulose, gelatin and proteins such as gamma globulins and fibrinogen. For example, Djerassi (U.S. Pat. No. 4,111,199) describes a multi-step leukopheresis process for preparing granulocytes. After collection, the blood is centrifuged and subsequently separated. The platelets and the plasma are further separated for re-infusion. The fraction containing the red cells and leukocytes is mixed with an HES solution in an external bag apparently in an open, septic system to sedimentate the red cells. The granulocytes reside in the remaining leukocyte fraction.

The blood donor in this process is a living person, while in the collection of cord blood the donor is not a person. Furthermore, although in Djerassi's process the final object is granulocyte preparation, also several components of the preceding processing steps are used (red cells and plasma are reinfused). Therefore, the sequence of the processing steps is defined in such a way as to prepare reinjectable components as well. In cord blood processing only the final preparation is important; resulting components from preceding steps are usually discarded. On the whole, Djerassi's process is not suitable for the preparation of stem cells from cord blood.

In the processing of blood, contamination with bacteria and fungi is a continuous concern. If a blood cell preparation is contaminated, it has to be regarded as not suitable for human use and should be discarded. Contamination must thus be prevented and the methods used in the collection and processing of blood must be as safe as possible. Aseptic handling must be reduced to a minimum to prevent contamination. For that reason, in general, closed bag systems are preferred, comprising several bags and connecting tubes. Blood can be transferred between the bags and tubes without aseptic procedures. With umbilical cord blood, contamination may occur during collection of the blood and the subsequent processing handling. Thus to prevent contamination, collection and processing of cord blood are preferably carried out in closed bag systems. However, in the current method for the processing of cord blood no such system is available. The red cell sedimentation solution has to be added through aseptic handling.

Figure 2:
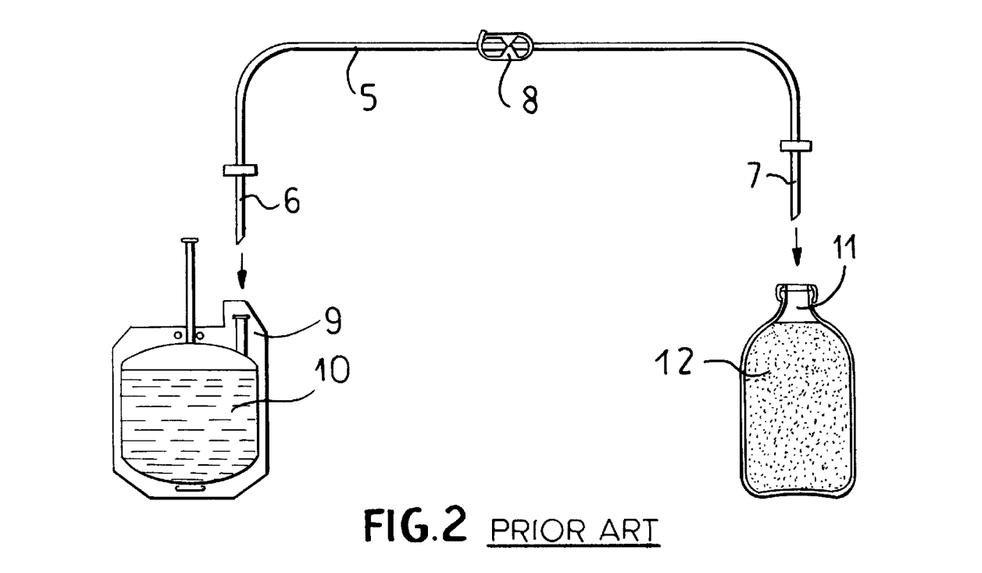
FIG. 2 is a diagram of another prior art system for adding a sedimentation fluid to collected blood.

HES solution is supplied by several manufacturers in a (usually 500 ml) container of glass or plastic. In general the HES concentration in this containers is 6%. Saline is added for isotonicity. A common method for adding the HES solution employs a transfer tubing system as shown in FIG. 2. The system consists of a tube 5 with two spikes, 6 and 7. and a clamp 8. First, clamp 8 is closed. Then, collection bag 9 with the blood 10 is entered with spike 6. Collection bag 9 is put on a balance. Now, HES container 11 is entered with spike 7. The required amount of HES solution 12 is added by opening clamp 8 and checking the balance. As an alternative, the HES solution can be taken from the HES container with a syringe and subsequently injected into the blood bag. Whichever method is chosen, all methods require at least two aseptic steps: entering the blood container and entering the HES container. Thus, in the current method for the processing of cord blood, the red cell sedimentation solution has to be added through aseptic handing, which increase the risk of contamination and thus discarding of the blood.

OBJECTS OF THE INVENTION

It is, therefore, the principal object of the present invention to provide an improved method of collecting and processing umbilical cord blood which will avoid the drawbacks of earlier systems and can simplify both the collection and treatment of the blood for sedimentation purposes.

It is another object of the invention to provide a blood collection process system which is particularly effective for the collection and processing of umbilical cord blood and especially for the collection of umbilical cord blood for long-term storage in cord blood banks and the like.

SUMMARY OF TEE INVENTION

The invention uses a closed, sterile bag system for the collection of cord blood and the subsequent addition of a red cell sedimentation solution. This bag system contains at least two separate compartments that are in temporary blocked communication, one containing the anticoagulant solution and the other containing the sedimentation solution. By removing the blockade these solutions can be brought together allowing for red cell sedimentation of the collected cord blood while maintaining the sterility of the system.

The compartments can be bags as in standard blood bag systems. The compartments can also be blocked sections of bags or of the tubes of blood bag system. The temporary blockade may be a break connector or a comparable component known in the art. Also, the temporary blockade may be a seal that can be opened from the outside. The system allows addition of the sedimentation solution to the cord blood in a closed system, thus avoiding cumbersome aseptic procedures and the chance of contamination. The procedure is safer and easier for handling than currently used methods.

More particularly, the method of the invention can comprise the steps of:

(a) providing a closed sterile collection bag system having at least two compartments including a compartment containing an anticoagulant and a compartment containing a red-cell sedimentation solution separated from a collection compartment by a removable blockage;

(b) admitting umbilical cord blood into the collection compartment and mixing the admitted umbilical cord blood with the anticoagulant; and (c) thereafter removing the blockage to contact the umbilical cord blood with the red-cell sedimentation solution entirely within the closed sterile collection bag system.

In apparatus terms the system can be a closed sterile collection bag system which comprises:

means forming at least two compartments including a compartment containing an anticoagulant and a compartment containing a red-cell sedimentation solution separated from a collection compartment;

a removable blockage between the compartment containing the red-cell sedimentation solution and the collection compartment; and means for admitting umbilical cord blood into the collection compartment for mixing of the admitted umbilical cord blood with the anticoagulant, whereby upon subsequent removal of the blockage the umbilical cord blood is contacted with the red-cell sedimentation solution entirely within the closed sterile collection bag system.

The erythrocyte sedimentation solution can contain hydroxyethylstarch (HES) or dextran in a concentration between 0.5 and 40% (preferably between 1 and 6%) and can be present in a volume of 8 to 1000 ml (preferably about 100 ml) the anticoagulant is preferably selected from the group which consists of ACD, CPD, CPDA, heparin and sodium citrate.

BRIEF DESCRIPTION OF THE DRAWING

The above and other objects, features, and advantages will become more readily apparent from the following description, reference being made to the accompanying drawing in which.

SPECIFIC DESCRIPTION

Figure 3:
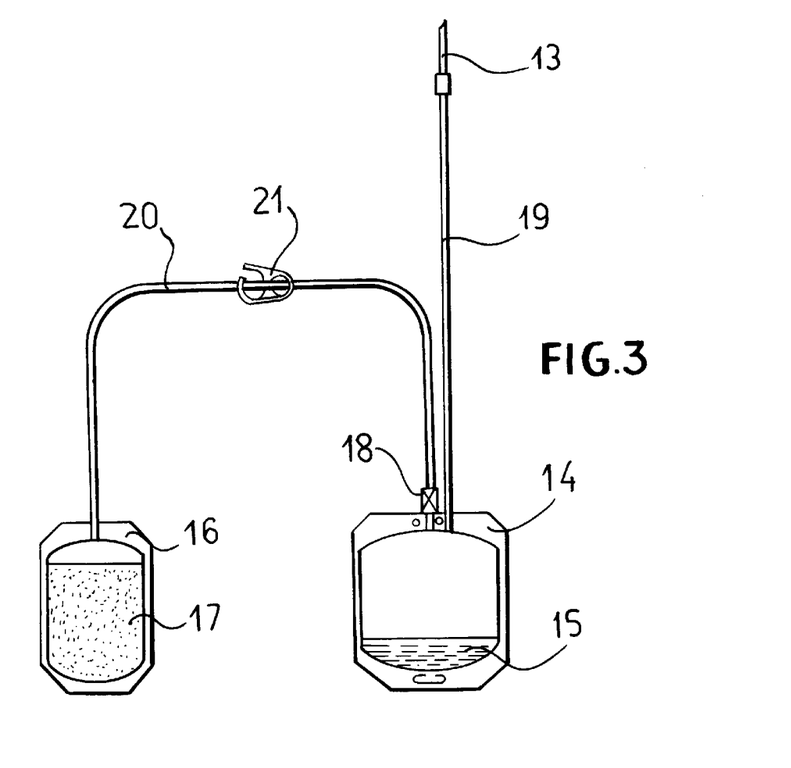
FIG. 3 is a diagram of the system of the invention in its most elementary form.

FIG. 3 shows the present invention in its most elementary form. The cord blood bag system consists of a collection needle 13, connected to collection bag 14 with CPD solution 15. Also connected to collection bag 14 is bag 16 containing the sedimentation solution 17. Sedimentation solution 17 is blocked from entering collection bag 14 by break connector 18. Blood is collected from the umbilical cord with needle 13 through tube 19 in collection bag 14. During collection the blood is mixed gently with CPD solution 15. After collection, tube 19 is sealed and disconnected. To sediment the red cells after blood collection, tube 20 is closed with clamp 21 and break connector 18 is opened. Collection bag 14 is put on a balance and the required amount of sedimentation solution is calculated. Clamp 21 is opened and the calculated amount of sedimentation solution 17 is introduced in collection bag 14. Finally, tube 20 is closed again with clamp 21. The collection bag, containing the cord blood and the required volume of the sedimentation solution, can now be left connected to the system or removed from the system for further processing.

Figure 4:
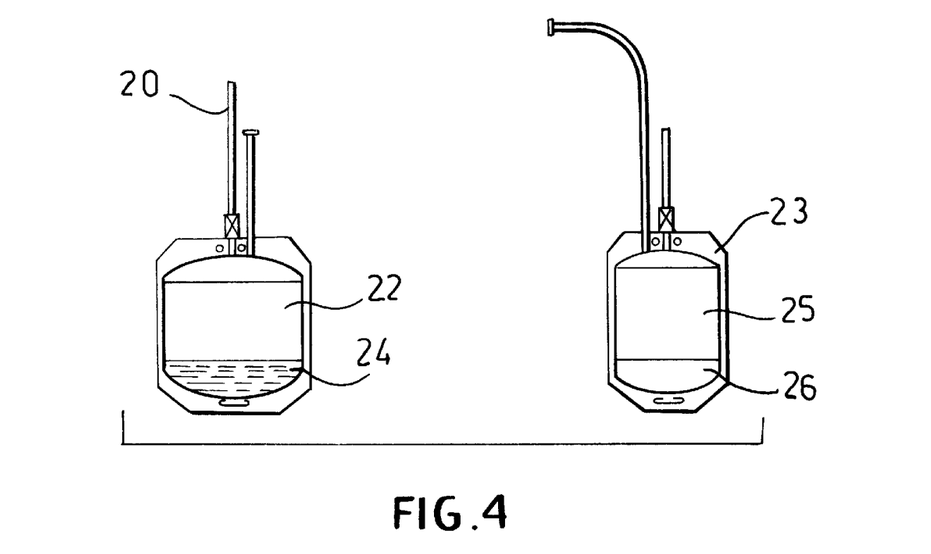
FIG. 4 illustrates processing of the sedimented blood with the system of IFG. 3.

In FIG. 4 an example of the subsequent processing is shown, being the separation of the various cord blood components after sedimentation. The leukocyte-rich plasma 22 is transferred via tube 20 to processing bag 23, leaving the sedimented red cells 24 behind. By the subsequent centrifugation step the leukocytes in processing bag 23 are spun down and the plasma 25 is removed. The cell preparation 26, containing the stem cells, is left in processing bag 23. After cryoprotectant is added to cell preparation 26, it is ready to be cryopreserved.

Figure 1:
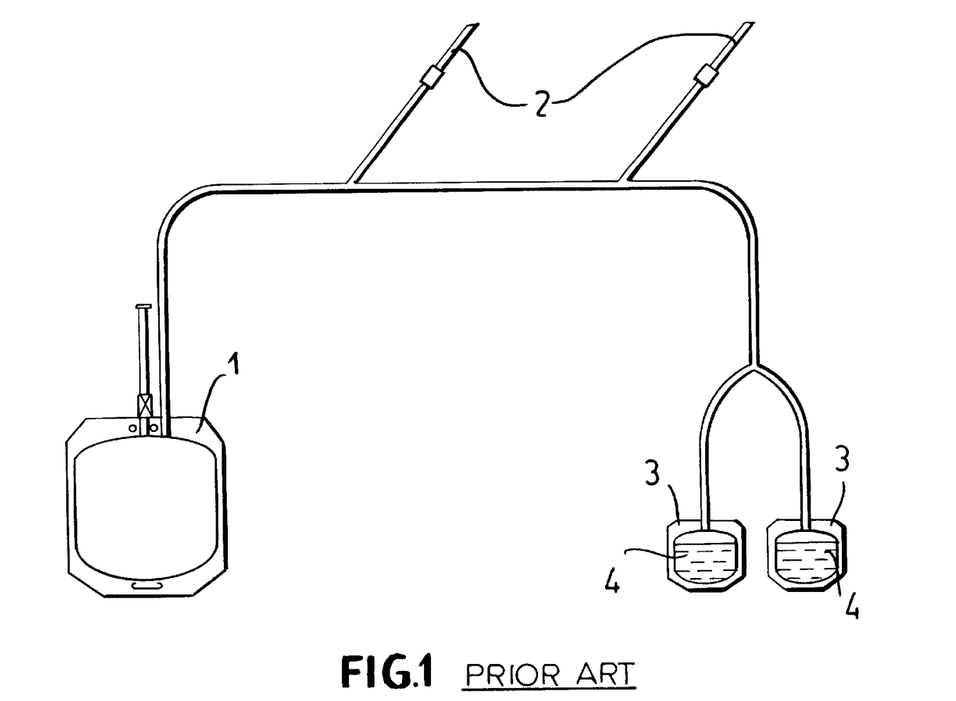
FIG. 1 is a diagram of a prior art blood collection system as has previously been described.
Figure 5:
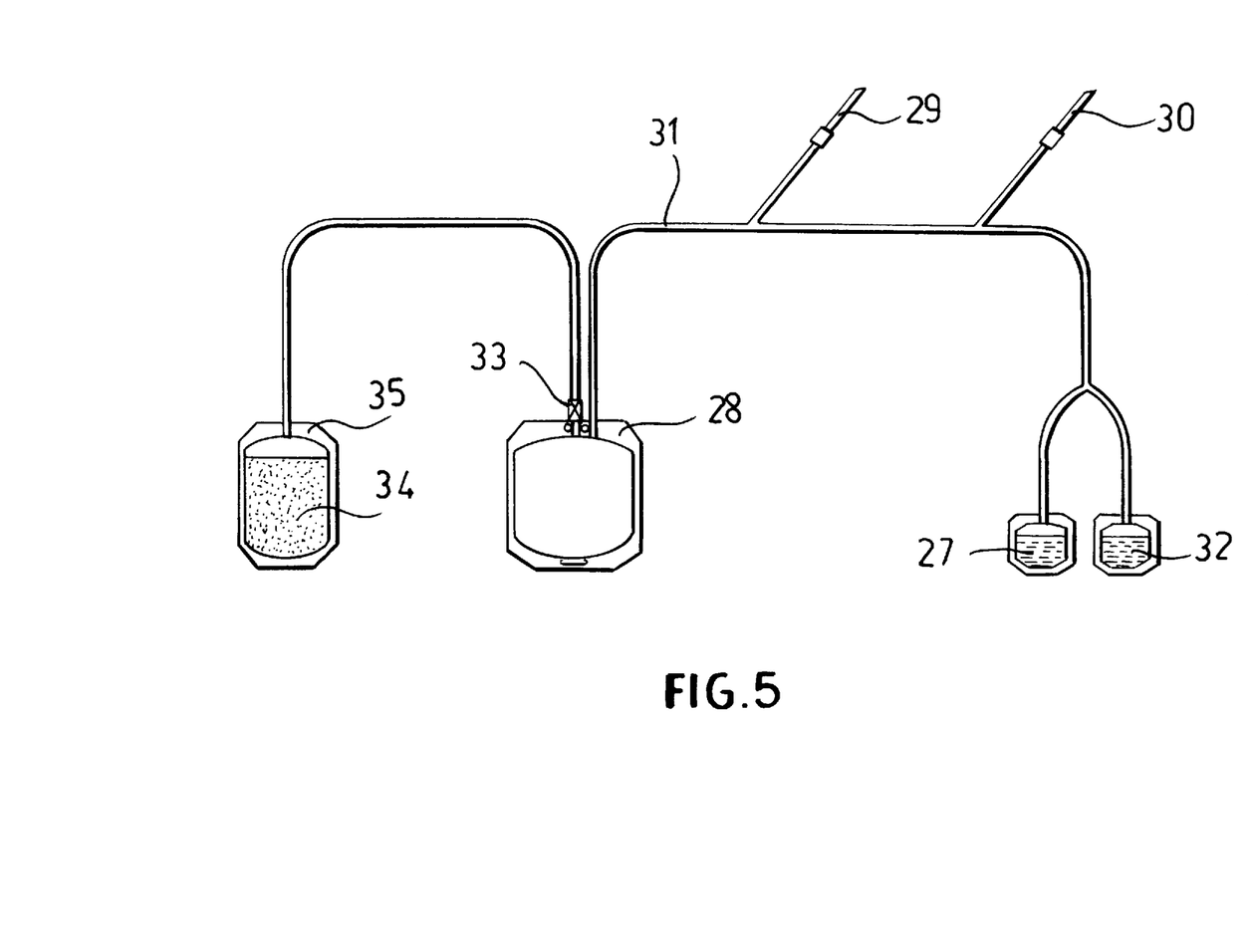
FIG. 5 is a diagram of a system analogous to that of FIG. 1 but provided with a compartment for the erythrocyte sedimentation solution in accordance with the present invention.

In FIG. 5 an extended version of FIG. 3 is shown, based on the cord blood bag system of NPBI (FIG. 1). Whereas in the system of FIG. 3 the CPD generally originates from a standard blood bag system, in FIG. 5 the CPD is contained in two separate bags, each filled with 15 ml of CPD. As the preferred ratio of anticoagulant and blood is 1:7, 15 ml of CPD is sufficient for the collection of approximately 100 ml of blood. Before collection, CPD solution 27 is introduced in collection bag 28. The cord blood is collected with the first needle 29. After closing needle 29, the second needle 30 is used. After the collection is completed, all the blood is collected in collection bag 28 by flushing the collection tube 31 with CPD solution 32. For further processing break connector 33 is opened and HES solution 34 from bag 35 is introduced into collection bag 28.

Figure 6:
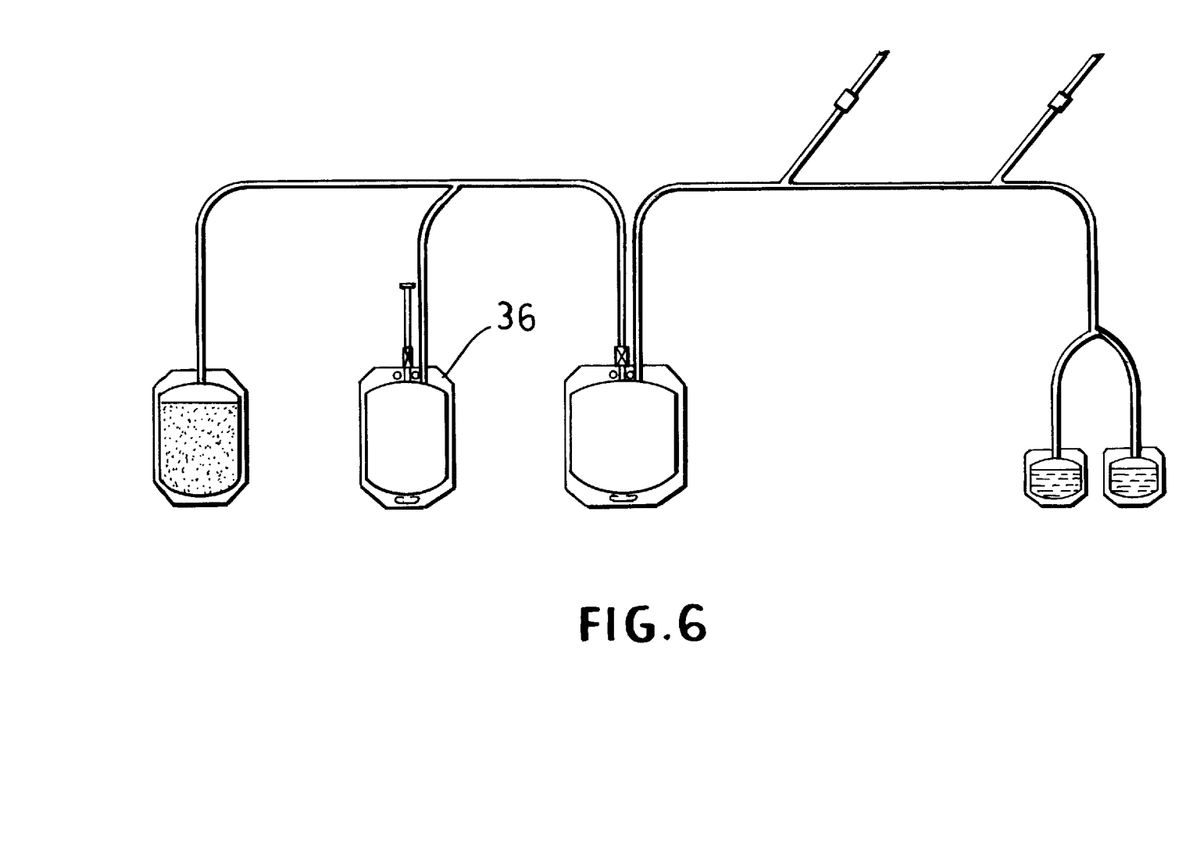
FIG. 6 is a diagram of a system similar to that of FIG. 5 but extended beyond that of FIG. 5 with respect to the means for processing the leukocyte-rich plasma after sedimentation.
Figure 7:
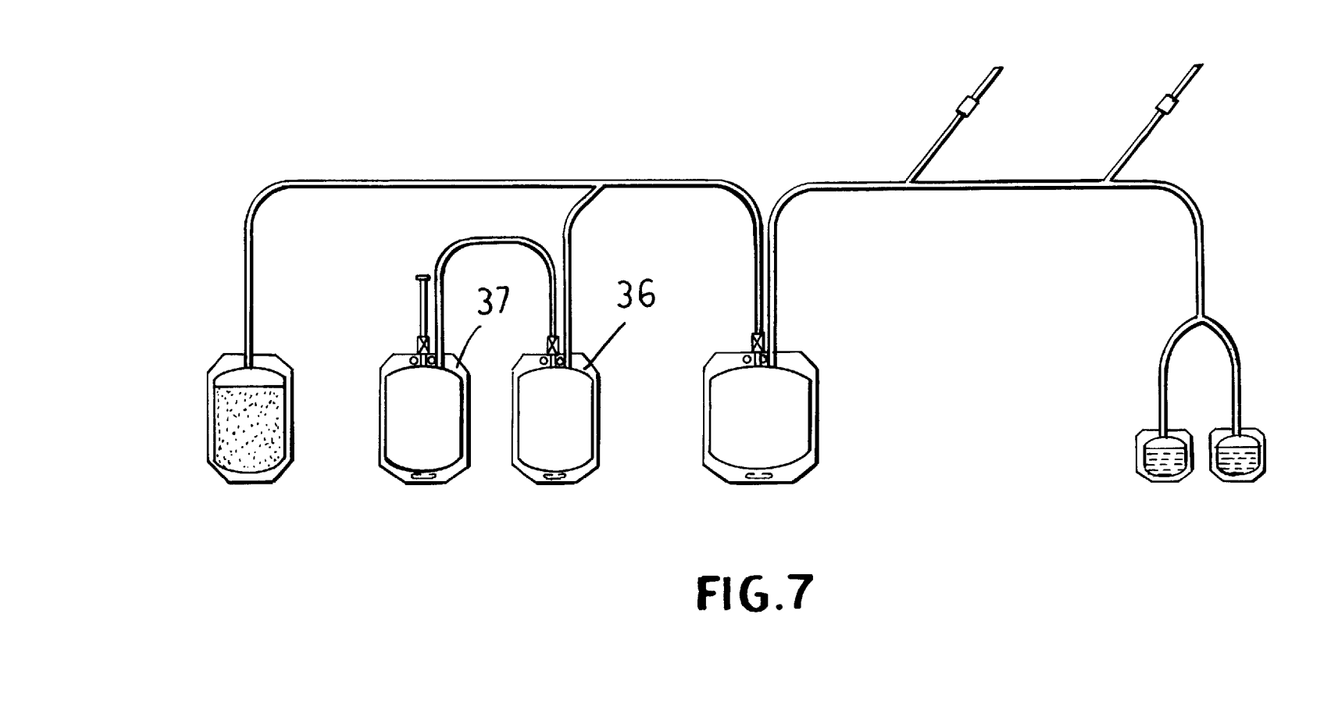
FIG. 7 is a diagram of a still more complex closed system for practicing the invention.

In FIG. 6 an even more extended system is shown, based on the system of FIG. 5. Now, processing bag 36 is added to the system. This bag can be used for the collection and the processing of the leukocyte-rich plasma after sedimentation and separation. In FIG. 7 an extra processing bag 37 is connected to processing bag 36. After the second centrifuge spin the leukocyte-free plasma can be transferred from processing bag 36 to processing bag 37.

All of the described systems are basically extensions of the system of FIG. 3 and form part of the same invention.

The essential feature of this invention is that a cord blood bag system consists of at least two compartments, one containing anticoagulant and one containing a red cell sedimentation solution, and that these compartments are in temporary blocked communication with each other.

It is generally advantageous to have the solutions in a temporarily blocked situation and not premixed. If the anticoagulant compartment would already contain the sedimentation solution, sedimentation would take place instantly during collection of the cord blood. This would segregate the blood suspension and could influence the blood collection process. Furthermore, it would influence sampling and the outcome of tests on the samples, such as tests for hematocrit. Finally, some tests itself could be influenced by the presence of sedimentation solution in the sample.

The described cord blood bag systems are assembled, filled with anticoagulant and sedimentation solution and subsequently sterilized and packaged at the manufacturer's. They are delivered in their sterile form at the transfusion center where the cord blood collection takes place.

The sedimentation solution in the described systems may vary in amount and concentration, depending upon the protocol of the transfusion center. Generally, the final HES concentration in the mixed blood product will be between 1 and 4%. In principle this can be achieved by many different concentrations and volumes of the HES solution. Concentrations between 1 and 40% and volumes between 10 and 1000 ml in the HES compartment can be used for the purpose.

Several other alternative embodiments of the present invention can be imagined, all of which would basically consist of a cord blood bag system with an anticoagulant solution and a red cell sedimentation solution in different compartments in temporary blocked communication, thus maintaining a closed sterile bag system for both cord blood collecting and processing.

Figure 8:
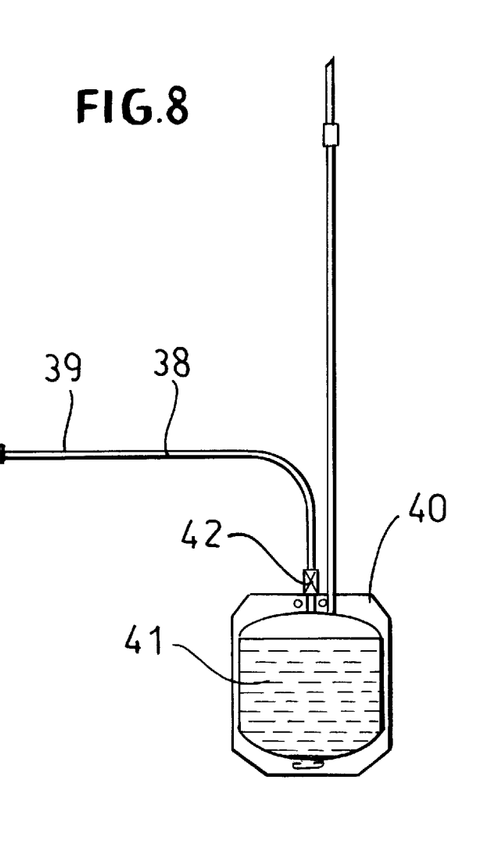
FIG. 8 is a diagram illustrating an alternative system according to the invention.

One of the alternative embodiments of the present invention is shown in FIG. 8, in which the HES solution 38 is contained in a sealed tube 39 connected to collection bag 40. After collection of the cord blood 41 break connector 42 is opened. The HES solution 38 can now be added to the collected blood 41. The tube can be equipped with markings indicating the relation between the volume of blood and the volume of HES solution that has to be added to reach a predetermined concentration in collection bag 40. Thus, there would be no need for a balance to determine and add the required volume of HES solution.

Figure 9:
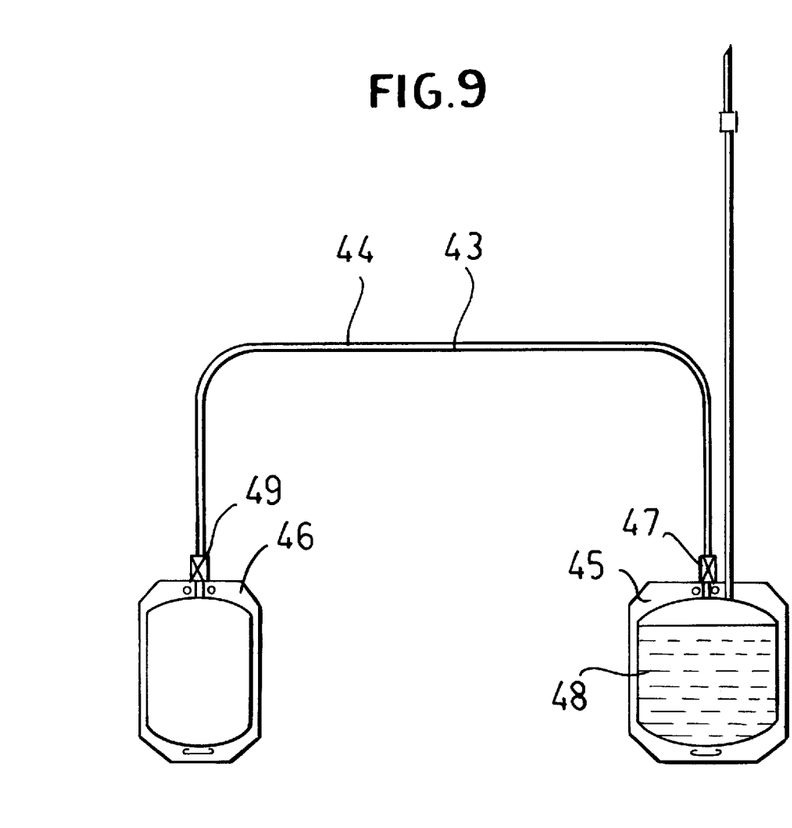
FIG. 9 is a diagram showing still another alternative.

Another alternative embodiment is shown in FIG. 9. The HES solution 43 can be contained in a tube 44 that connects the collection bag 45 and the processing bag 46. By opening break connector 47 HES solution 43 can be added to the collected blood 48. After sedimentation, break connector 49 can be opened and the leukocyte-rich plasma can be transferred to processing bag 46 through tube 44.

Figure 10:
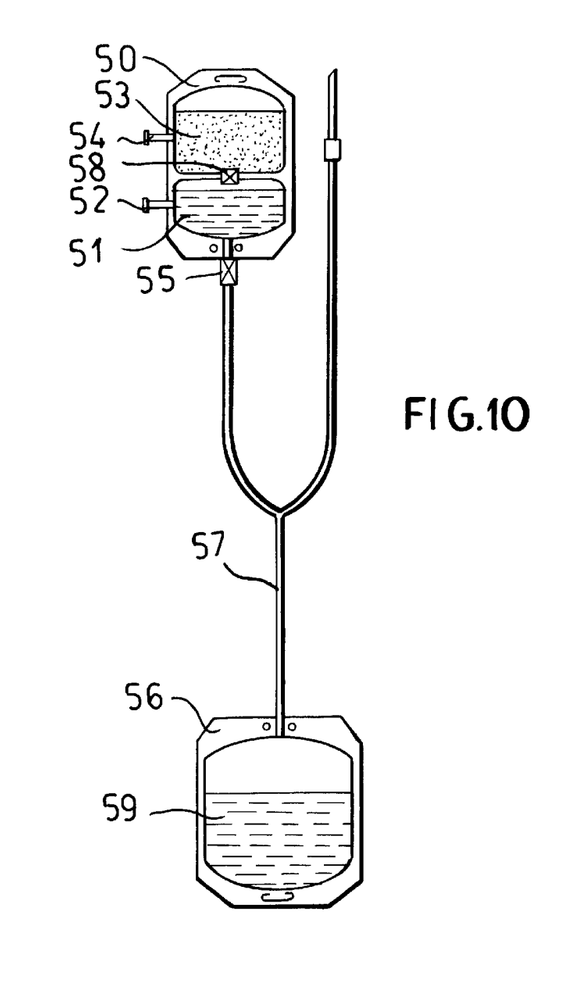
FIG. 10 is a diagram of a system according to the invention utilizing a multicompartment bag.

In yet another alternative embodiment, the HES solution and CPD solution are contained in two different compartments that form a part of a single bag; a dual compartment container. Several designs of such containers are known in the art. An example is shown in FIG. 10. Dual compartment bag 50 is filled with CPD 51 via tube 52 and with HES solution 53 via tube 54 and the system is subsequently sterilized. Before cord blood collection, temporary blockade 55 is removed and CPD 51 enters the collection bag 56 through tube 57. After collection, blockade 58 is removed and via tube 57 the HES solution 53 can be added to the collected blood 59. Further processing proceeds as described earlier.

Figure 11:
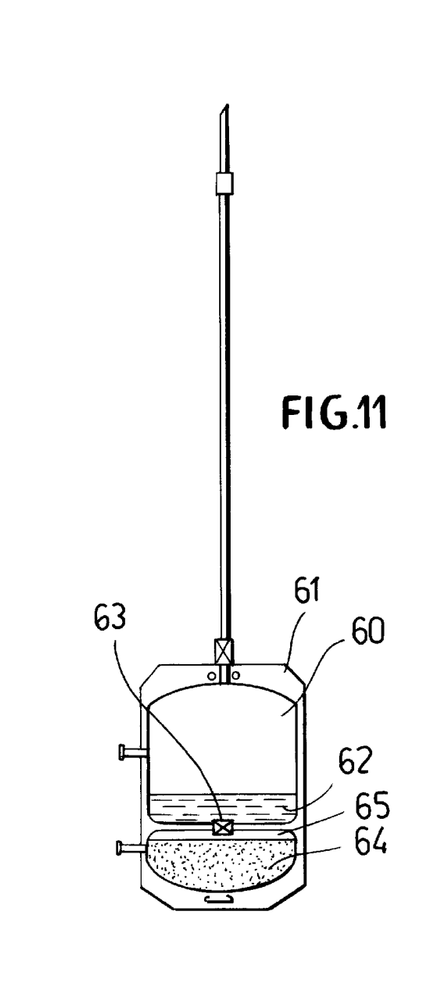
FIG. 11 is a diagram of a variant of this embodiment.

A variant on this embodiment is shown in FIG. 11, where the cord blood is collected in the upper compartment 60 of collection bag 61. This compartment also contains the CPD 62. After collection temporary blockade 63 can be removed and the HES solution 64 in lower compartment 65 can be added to the collected blood in the upper compartment.

As the CPD solution and the HES solution are in different compartments of the same system in temporary blocked communication, both the collection and the red cell sedimentation can be carried out in one closed system. Therefore, the risk of contamination of the final stem cell preparation is considerably reduced. Less preparations will have to be discarded because of contamination. Also, the handling of the processing bags and the solutions is simplified. On the whole, the efficiency of the processing procedure of stem cells will improve. Also, the handling of the processing bags and solutions is simplified. On the whole, the efficiency of the processing procedure of stem cells will improve.

Wherever the words "HES" and "dextran" are used in the above text, the words "red cell sedimentation solution" can also be read, not to limit the applicability of the present invention. Wherever the words "break connector" are used, the words "temporary blockade" are indicated at the same time.

It will be clear for those skilled in the art, that other embodiments/extensions can be imagined, based on the principle of the application and are regarded as part of the present invention.

We claim:

1. A method of collecting umbilical cord blood comprising the steps of:
   (a) providing a closed sterile collection bag system having at least two compartments, one of said compartment containing an anticoagulant and another of said compartment containing a red-cell sedimentation solution, said system having a collection compartment which is separated from the compartment containing the red-cell sedimentation solution by a removable blockage;
   (b) admitting umbilical cord blood into said collection compartment and mixing the admitted umbilical cord blood with said anticoagulant; and
   (c) thereafter removing said blockage to contact the umbilical cord blood with said red-cell sedimentation solution entirely within said closed sterile collection bag system.

2. The method defined in claim 1 wherein said solution contains hydroxyethylstarch in a concentration between 0.5 and 40% and in a volume of 8 to 1000 ml.

3. The method defined in claim 2 wherein said solution contains hydroxyethylstarch in a concentration between 1 and 6% and in a volume of about 100 ml.

4. The method defined in claim 1 wherein said solution contains dextran in a concentration between 0.5 and 40% and in a volume of 8 to 1000 ml.

5. The method defined in claim 4 wherein said solution contains dextran in a concentration between 1 and 6% and in a volume of about 100 ml.

6. The method defined in claim 1 wherein said anticoagulant is selected from the group which consists of heparin anticoagulant citrate-dextrose, citrate-phosphate-dextrose, citrate-phosphate-dextrose-adenine and sodium citrate in solution.

7. The method defined in claim 1 wherein said one compartment is the same compartment as said collection compartment.

8. A closed sterile collection bag system for collecting umbilical cord blood, said collection bag system comprising:
   means forming at least two compartments, one of said compartment containing an anticoagulant and a compartment containing a red-cell sedimentation solution containing hydroxethylstarch or dextran, said system having a collection compartment which is separated from the compartment containing the red-cell sedimentation solution;
   a removable blockage between said compartment containing said red-cell sedimentation solution and said collection compartment; and
   means for admitting umbilical cord blood into said collection compartment for mixing of the admitted umbilical cord blood with said anticoagulant, whereby upon subsequent removal of said blockage the umbilical cord blood is contacted with said red-cell sedimentation solution within said closed sterile collection bag system.

9. The closed sterile collection bag system for collecting umbilical cord blood defined in claim 8 wherein said solution contains hydroxyethylstarch in a concentration between 0.5 and 40% and in a volume of 8 to 1000 ml.

10. The closed sterile collection bag system for collecting umbilical cord blood defined in claim 9 wherein said solution contains hydroxyethylstarch in a concentration between 1 and 6% and in a volume of about 100 ml.

11. The closed sterile collection bag system for collecting umbilical cord blood defined in claim 8 wherein said solution contains dextran in a concentration between 0.5 and 40% and in a volume of 8 to 1000 ml.

12. The closed sterile collection bag system for collecting umbilical cord blood defined in claim 11 wherein said solution contains dextran in a concentration between 1 and 6% and in a volume of about 100 ml.

13. The closed sterile collection bag system for collecting umbilical cord blood defined in claim 8 wherein said anticoagulant is selected from the group which consists of heparin anticoagulant citrate-dextrose, citrate-phosphate-dextrose, citrate-phosphate-dextrose-adenine and sodium citrate in solution.

14. The system defined in claim 8 wherein said one compartment is the same as said collection compartment.

15. The system defined in claim 8 wherein said collection compartment is a compartment other than said one compartment and said other compartment.

* * * * *